United States Patent [19]

Nagao

[11] Patent Number: 4,784,770

[45] Date of Patent: Nov. 15, 1988

[54] METHOD FOR PRODUCING METHANE GAS

[76] Inventor: Masamichi Nagao, 87-302 Ikidanchi Nishi-Ku, Fukuoka, Japan

[21] Appl. No.: 864,082

[22] Filed: May 16, 1986

[30] Foreign Application Priority Data

May 17, 1985 [JP] Japan .............................. 60-103882

[51] Int. Cl.$^4$ ........................................... C02F 11/04
[52] U.S. Cl. ...................................... 210/603; 210/773
[58] Field of Search .............. 210/603, 631, 773, 173, 210/174, 609, 613

[56] References Cited

U.S. PATENT DOCUMENTS

| 4,369,194 | 1/1983 | Arsovic | 210/603 X |
| 4,375,412 | 3/1983 | Schimel | 210/603 |
| 4,400,195 | 8/1983 | Rijkens | 210/603 X |
| 4,511,370 | 4/1985 | Hunziker et al. | 210/603 X |

Primary Examiner—Tom Wyse
Attorney, Agent, or Firm—Steinberg & Raskin

[57] ABSTRACT

A method and apparatus for producing methane gas from organic solid materials in existence in industrial and living wastes, in which the oganic materials are finely ground by milling while water or organic suspension is added by injection in order to prepare a slurry, in which the slurry is deaerated to obtain raw liquid for generating methane gas in high concentration, and in which the digestive tank receives the raw liquid with treating by anaerobic bacteria to generate the methane gas.

5 Claims, 5 Drawing Sheets

METHOD FOR PRODUCING METHANE GAS

BACKGROUND OF THE INVENTION

The present invention relates to a method and apparatus for producing methane gas from organic solid materials in existence in industrial and living wastes.

A conventional method for producing methane gas has been developed, in which a sewage waste water is treated aerobically and the methane gas is collected from a disposal residue. However, in this case, since a weight ratio of an organic material with reference to the water is extremely small, the concentration of the organic material flowing or dissolving in the water is small, and thus it may stay in a digestion or fermentation tank for a long time. Accordingly, in this embodiment, the digestive tank and supplementary equipments are enlarged, and hence the installation space of the apparatus becomes large. Therefore, the cost of the apparatus becomes high, and the gas is not produced effectively as well as it is difficult to maintain the apparatus.

Another conventional method for producing methane gas has been proposed, in which the organic material obtained from an industrial waste is treated anaerobically. However, in this case, the applicable organic materials are restricted to the special materials, for example, wastes of the food industry such as wastes produced by a brewage, and liquids obtained by filtering solids in excretions of cattle, and consequently this method cannot be applied to all organic materials, lack of universality. Further, in this embodiment it takes a quite long time to generate the gas and the produced gas is less. Further, it is widely well-known that the high temperature treatment at 53° C. is effective in order to conduct the fermentation effectively, however, the digestive tank is enlarged. Hence, it is difficult economically to completely make an adiabatic surface to the digestive tank, and hence the effective production of the methane gas cannot be realized practically.

In addition, in case of a large-sized digestive tank, the installation cost of the apparatus is enlarged for the strength of the groundwork and for manufacturing the body of the digestive tank as well as the long construction period, with the result of the disadvantageous account balance.

SUMMARY OF THE INVENTION

Accordingly, it is an object of the present invention to provide a method and apparatus for producing methane gas from organic solid materials in existence in industrial and living wastes, free from the aforementioned defects and disadvantages, which is capable of producing the methane gas in a short time effectively and economically.

It is another object of the present invention to provide a method and apparatus for producing methane gas, which is capable of advantageously utilizing the produced methane gas as the fuel instead of the petroleum.

It is further object of the present invention to provide a method and apparatus for producing methane gas, which is capable of effectively producing the methane gas of high quality in a high yielding rate, and which is capable of minimizing the disposal residue.

It is still another object of the present invention to provide a method and apparatus for producing methane gas, which can be realized readily and easily at a low cost.

In accordance with one aspect of the invention, there is provided a method for producing methane gas, comprising milling an organic material into fine particles, while water or organic suspension is added to prepare slurry, deaerating the slurry to obtain raw liquid for generating methane gas high concentration, feeding the raw liquid to a digestive tank, and treating the raw liquid in the digestive tank by anaerobic bacteria to generate the methane gas.

In accordance with another aspect of the invention, there is provided an apparatus for producing methane gas, comprising means for milling an organic material into fine particles, means for injecting water or organic suspension to the mill means to prepare a slurry, means for deaerating the slurry to obtain raw liquid for generating methane gas in high concentration, a digestive tank for treating the raw liquid by anaerobic bacteria to generate the methane gas, and means for feeding the raw liquid from the mill means to the digestive tank.

In a preferred embodiment, the organic material is finely ground by a colloidal mill to approximately 1–50 microns.

In another preferred embodiment, the digestive tank comprises a pair of or a plurality of tank units, and the tank unit having an upright cylindrical form possesses its outer diameter ranging 2.2–3.0 meters and its height ranging 5.5–10.5 meters.

Other and further objects, features and advantages of the invention will appear more fully from the following description with reference to the accompaying drawings, in which:

DESCRIPTION OF THE PREFERRED EMBODIMENTS

Figure 1:
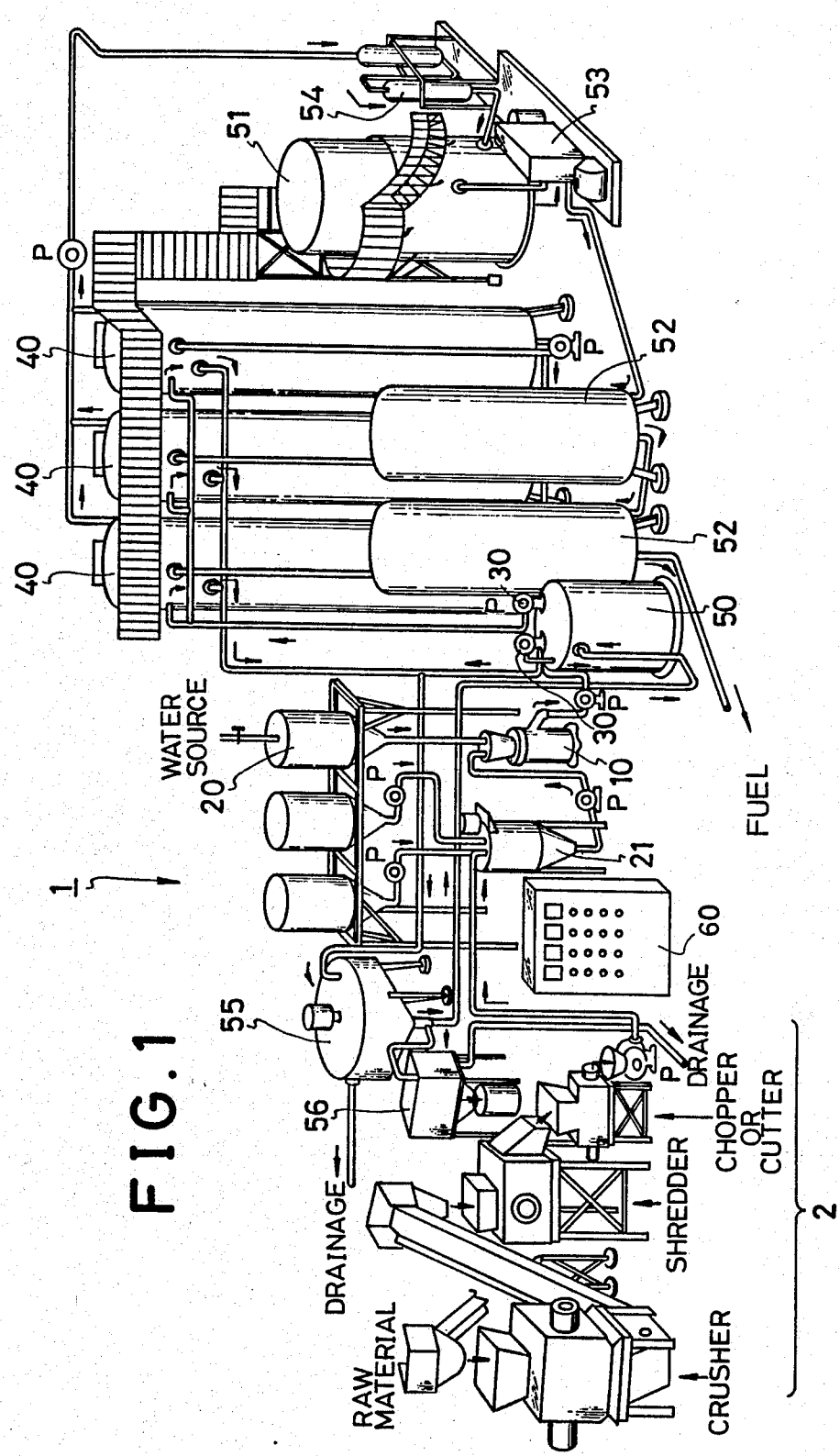
FIG. 1 is a perspective view of an apparatus for producing methane gas according to the present invention.

Referring now to the drawings, wherein like reference numerals denote like parts throughout different figures, there is shown in FIGS. 1–4 an apparatus for producing methane gas according to the present invention.

In the drawings, the methane gas producing apparatus 1 according to the present invention includes pulverizing means 2 for pulverizing organic solid materials such as vegetable solids and raw bone of cattle and sea products into rough pieces, mill means 10 for milling the rough particles pulverized by the pulverizing means 2 into fine particles, an injecting means 20 for injecting water or organic suspension such as waste milk, waste vegetable juice into the mill means 10 to prepare slurry, a deaerating means 30 for deaerating the slurry to obtain raw liquid for generating methane gas, and a digestive tank 40 for treating the raw liquid fed from the mill means 10 in an anaerobic digestion or fermentation by anaerobic bacteria to generate the methane gas.

The pulverizing means 2 roughly pulverizes the organic solid materials into at most 5 mm$^3$ so that the mill means 10 may readily catch the pulverized organic solid materials. When the vegetable organic solid materials are pulverized, a shredder or a cutter is used. When the large-sized organic solid materials are pulverized, a crusher, the shredder or a meat chopper is used. Accordingly, organic solid materials such as waste oil and theriac or syrup are fine particles, and thus there is no need for such materials passing through the pulverizing means 2.

Figure 2:
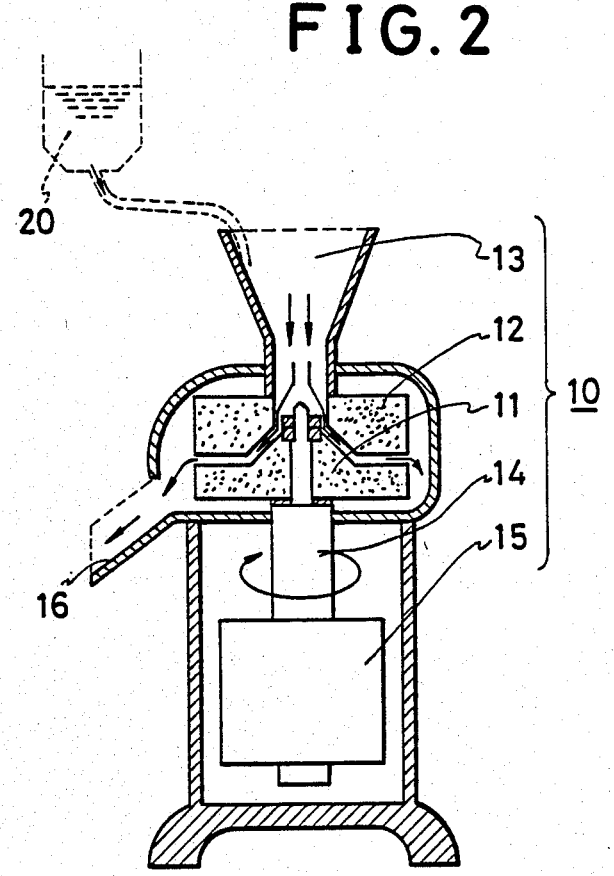
FIG. 2 is a longitudinal cross sectional view of a mill means shown in FIG. 1.
Figure 3:
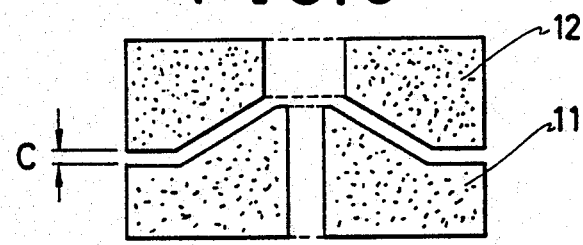
FIG. 3 is a longitudinal cross sectional view of rotary and fixed discs of the mill means of FIG. 2.

The mill means 10 further finely grinds the organic solid materials which are pulverized by the pulverizing means 2, and various wet fine pulverizers can be used. In this preferred embodiment, a colloid mill shown in FIG. 2 is used as the mill means 10. The colloid mill 10 includes a pair of rotary disc 11 and fixed disc 12 facing to each other, as shown in FIG. 3. The clearance C between milling surfaces of the two discs 11 and 12 is so determined to 10–100 microns that the organic solid materials obtained from an industrial or living waste or a sewage waste water disposal may be milled approximately to 1–50 microns of fine particles. The milling surface of the rotary disc 11 is made of diamond, boron nitride, or the like, and the surface of the fixed disc 12 is made of new ceramic material, or the like. The clearance between the two discs 11 and 12 may be determined depending on the nature of the organic materials, the treating or passing speed through the clearance, and so forth. When the mill means 10 mill or finely grind the organic solid materials, water or organic suspension is added to the mill means 10 by the injection means 20 to prepare a slurry.

In FIG. 2, the mill means 10 further comprises a hopper 13 for receiving the raw material to be supplied, a rotary shaft 14 for rotating the rotary disc 11, drive means 15 connecting the rotary shaft 14, and a discharge chute 16.

When one or at least two kinds of organic solid materials supplied from the inlet hopper 13, and an enzyme may be supplemented simultaneously for promoting the decomposition of the organic solid materials, pass through the clearance between the discs 11 and 12 together with the water or the organic suspension injected from the injection means 20, the organic solid materials contact microbites formed on the surfaces of the discs 11 and 12, thereby being milled into fine particles. In the same time, the milled organic solid fine particles are completely admixed with thawater or the organic suspension to prepare slurry in which the milled organic materials are suspended or dissolved in the liquid, and the slurry is discharged from the chute 16 by virture of the centrifugal force.

In this case, since the clearance of 10–100 microns between the two discs 11 and 12 also functions as a screen, the milled organic particles discharged from the mill means 10 in the slurry state possess approximately 1–50 microns of size. Hence, when touching such slurry by fingers, it does not feel rough at all. The water or organic suspension added to the mill means 10 functions not only the solvent of the organic materials but also a lubricant for milling and a coolant for the mill means 10.

The slurry discharged from the mill means 10 is fed to the digestive tank 40 via a storage tank 50 in which the slurry is once stored and is deaerated by deaerating means 30 such as a vacuum pump p connected to the storage tank 50 for removing the air.

In a preferred embodiment, the digestive tank comprises a pair of or a plurality of digestive tank units aligned either in series or in parallel, installed directly on the ground, and the tank unit having an upright cylindrical form may be manufactured, having a ratio of its outer diameter to its height of one to 2.5–3.5, of which the outer diameter ranges between 2.2–3.0 meters and the height ranges between 5.5–10.5 meters.

In FIGS. 1–4, numeral 21 denotes a mixing tank in which the organic solid materials to be supplied to the mill means 10 are blended. Numerals 51, 52, 53 and 54 designate a gas holder for storing the methane gas generated in the digestive tank 40, a gas receiver, a compressor and a desulfurizer tower, respectively. Numerals 55 and 56 denote a separation precipitation tank and a dehydrator, respectively, and numeral 60 designates a controller for controlling the mill means 10, the injection means 20, the mixing tank 21, the digestive tank 40, the storage tank 50, the gas holder 51, the gas receiver 52, the compressor 53, a fuel tank, and so forth.

Figure 4:
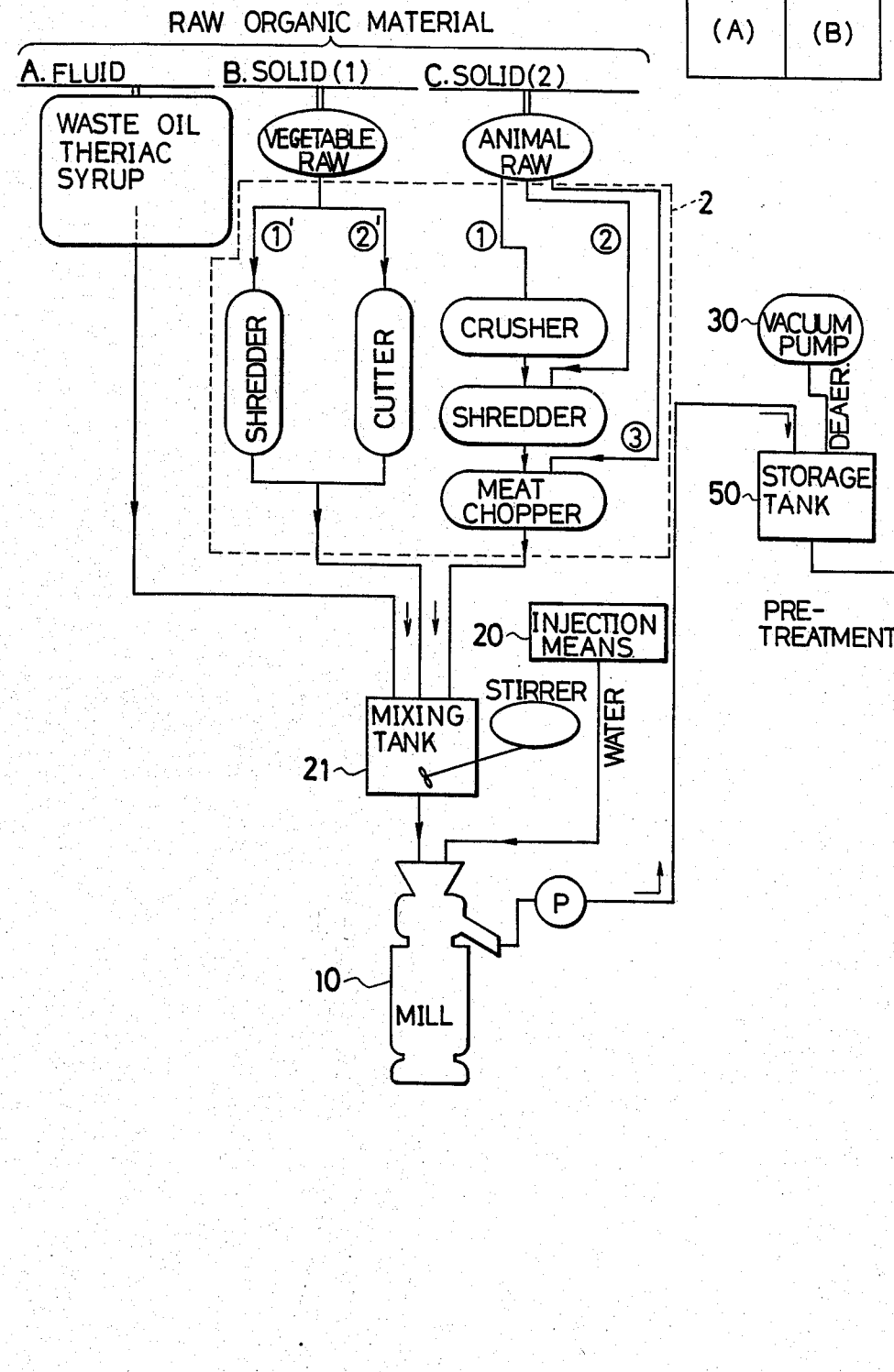
FIG. 4 is a flow chart of the apparatus shown in FIG. 1 for explaining a method for producing methane gas according to the present invention.
Figure 4B:
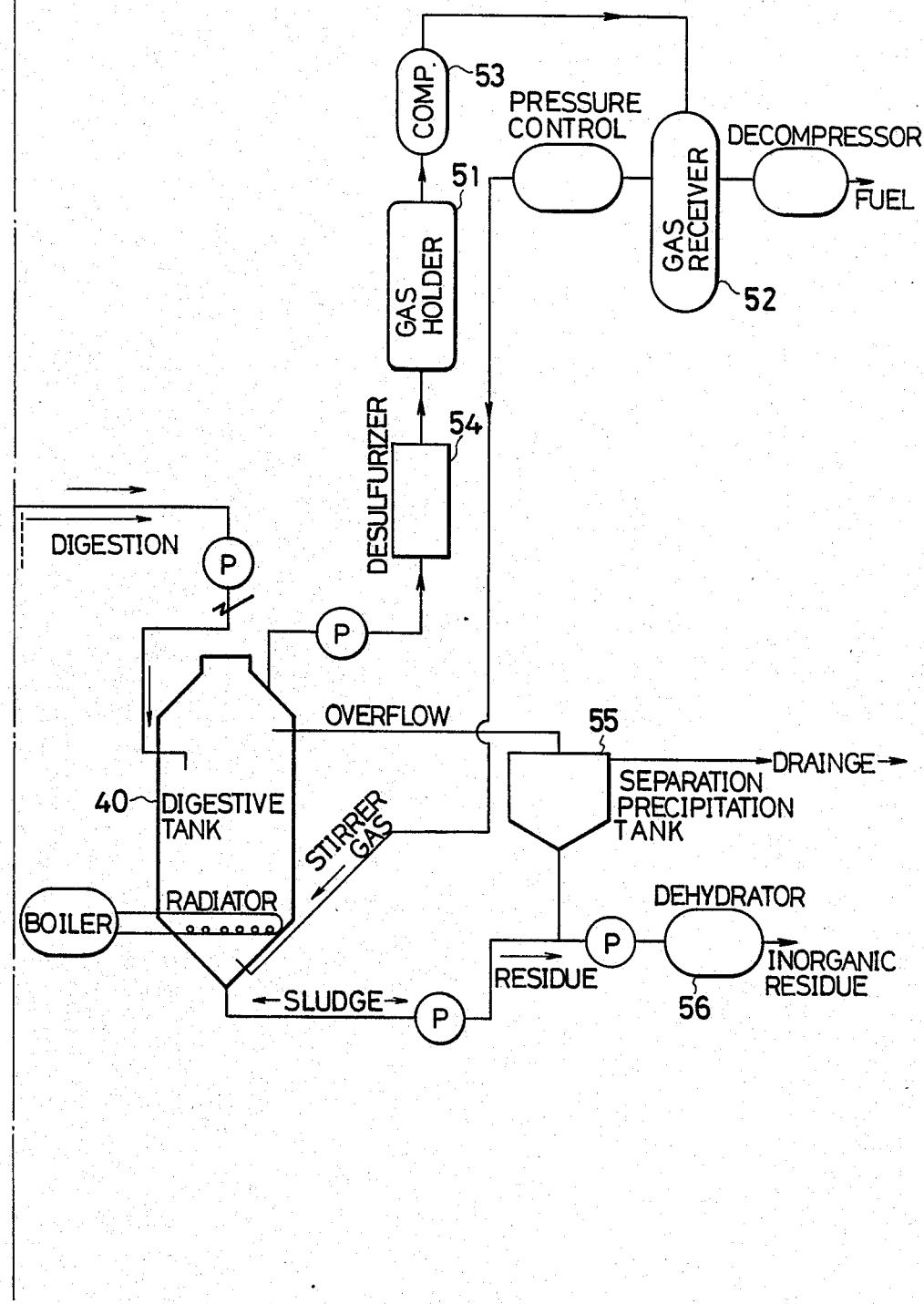

Next, a method for producing methane gas according to the present invention will now be described in connection with FIG. 4. First, one or at least two kinds of organic solid materials such as animal proteins, fats, vegetable carbohydrates and fibers, which may be raw, heated, water-contained and dried, are passed through the pulverizing means 2 to roughly pulverize into the organic solid particles of at most 5 mm$^3$ size, and then the pulverized organic solid particles are passed through the mill means 10 having a pair of discs 11 and 12 to further mill into fine particles of 1–50 microns, resulting in that the surface areas of the organic solid materials may be increased and that the cell walls of the organic solid materials may be destroyed so that the bacteria may readily digest the substances in the cells.

When the organic materials are milled by the mill means 10, a proper amount of water or organic suspension is controlled to be added to the mill means 10 from the injection means 20 so that the mixing ratio between the organic material and the water in the liquid discharged from the chute 16 of the mill means 10 may be 1:4–1:20 by weight. Consequently, the liquid discharged from the chute 16 of the mill means 10 becomes the slurry. In this case, the water or organic suspension to be added is controlled within the above noted ratio by weight depending on the viscosity and the particle size of the organic solid materials and the sludge concentration in the digestive tank 40. Then the slurry is fed to the storage tank 50 while the air bubbles admixed in the liquid at the mill means 10 are removed by the deaerating means 30 so as not to prevent the anaerobic digestion or fermentation, thereby obtaining the raw liquid for generating the methane gas in high concentration. Such a raw liquid is fed to the digestive tank 40 and the anaerobic digestion or fermentation is conducted in existence of the methane bacteria in the digestive tank 40 to generate the methane gas.

The raw liquid in the storage tank 50 is fed to the digestive tank 40 corresponding to the variation (digestion condition of nutriment) of the liquid quality concentration (weight ratio between the water and the organic substance is 80–95 to 20–5) in the digestive tank 40, and the raw liquid is decomposed by the bacteria in the digestive tank 40 to generate the methane gas. As shown in FIG. 4, then the generated methane gas in the digestive tank 40 is sent to the gas holder 51 via the desulfurizer tank 54 and is stored there. Then, the methane gas is compressed by the compressor 53 and the compressed methane gas is collected in the gas receiver 52. The compressed methane gas in the gas receiver 52 is decompressed for using as the fuel. The lees of the digestion in the digestive tank 40 is discharged as the digestive sludge which is dehydrated by the dehydrator 56 to obtain an inorganic residue for fertilizer.

In the decomposition activity of the organic material by the methane bacteria, a carbon nitrogen ratio (C/N ratio) is important. The carbon may be the energy source and the nitrogen may be nutritive elements. When the carbon nitrogen ratio (C/N ratio) between the sugar and the fat for the carbon source and the protein for the nitrogen source is approximately 14, the maximum amount of carbon is gasified. On the other hand, as regards the decomposing speed of the organic material, the carbohydrate is fastest, next the fat, and the protein is slowest. Regarding the decomposing limit, the protein is smaller than the fat. Accordingly, in order to prepare the raw liquid for generating the methane gas, in addition to the protein organic material including much nitrogen and the vegetable organic material including much carbohydrate, the fat including much carbon is preferably added.

Figure 5:
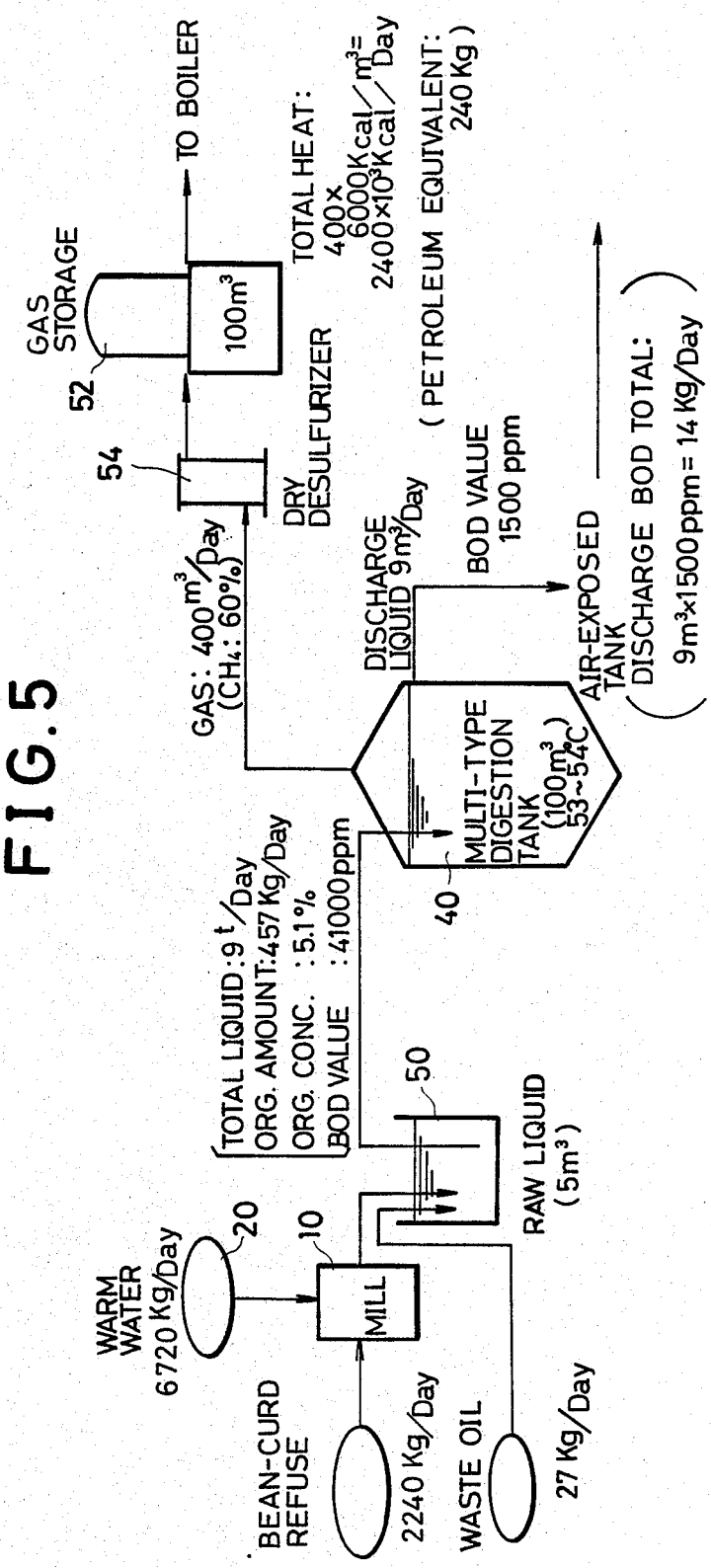
FIG. 5 is a schematic view of one example of the method according to the present invention.

Next, the methane gas is produced according to the present method by using bean-curd refuse obtained in a bean-curd production process and its result is shown in Table 3, as shown in FIG. 5. The bean-curd refuse together with a little amount of waste oil of fried bean-curd admixed thereto is passed through the mill means 10 while the water is added to the mill means 10 from the injection means 20 to obtain the slurry.

EXAMPLE

The methane gas is produced by using the discharged waste from a bean-curd factory.

Discharged waste amount:
The discharged bean-curd refuse amount is:

160 kg×14 *drums*=2240 kg/day (*containing 80% of water*)

One drum contains 160 kg of bean-curd refuse.
The bean-curd solid:

2240 kg×0.2=448 kg/day

The total organic solid material amount is calculated in the following according to Table 1:

448 kg×0.96=430 kg/day

Methane gas digestive tank capacity:
Considering that the organic material disposal amount in the high temperature fermentation at 53°–54° C. is 5 kg/m$^3$/day, 430/5=86 m$^3$ (*actual liquid amount*)

This can be compressed to 430/7=61 m$^3$ by strictly controlling.

TABLE 1

| (Components of bean-curd refuse) | | |
|---|---|---|
| Component | Content (%) (dry) | |
| Protein | 25 | Total amount |
| Sugar | 34 | of organic |
| Fat | 19 | material |
| Fiber | 18 | 96% |
| Ash | 4 | |

Considering 10% of volume of the upper space part of the digestive tank, the total capacity of the digestive tank is 95 m$^3$, and the digestive tank comprises three upright cylindrical tank units (one tank unit capacity is approximately 33 m$^3$).

Dilute warm water:
Three times of dilute warm water with respect to the bean-curd refuse is used:

2240 kg×3=6720 kg/day

Therefore, the total liquid amount is:

240+6720=8960 kg/day (When specific gravity is approximately one, this amount is approximately 9 m$^3$/day, which is supplied into the digestive tank every day.)

Produced methane gas amount:
The produced methane gas amounts per components are shown in Table 2.

TABLE 2

| Component | Generated gas amount per 1 kg substrate | CH$_4$ (%) |
|---|---|---|
| Protein | 950 liter | 55 |
| Sugar | 950 | 55 |
| Fat | 1000 | 80 |
| Fiber | 800 | 55 |

Therefore, the produced gas amounts per day are in the following Table 3.

TABLE 3

| | Discharged amount (kg/day) | Generated gas (m$^3$/day) | Generated CH$_4$ (m$^3$/day) | CH$_4$ (%) |
|---|---|---|---|---|
| Protein | 448 × 0.25 = 112 | 112 × 950 = 106 | 106 × 0.55 = 58 | |
| Sugar | 448 × 0.34 = 152 | 152 × 950 = 144 | 144 × 0.55 = 79 | |
| Fat | 448 × 0.19 = 85 | 85 × 1000 = 85 | 85 × 0.8 = 68 | |
| Fiber | 448 × 0.18 = 81 | 81 × 800 = 65 | 65 × 0.55 = 36 | |
| Total | | 400 m$^3$/day | 241 m$^3$/day | 60% |

The methane gas containing rate in the total gas obtained at the end is 60%.

It is readily understood from the description of the preferred embodiments of the present invention, that the organic solid materials which can hardly be used for the raw material, can be utilized as the methane gas generating raw material by roughly pulverizing and then finely milling in the liquid to prepare the slurry, which is very advantageous from the point of the resource utilization, and that, since the slurry is so smooth that no roughness may be felt by fingers and the surface areas of the organic solid materials are very much enlarged, the organic solid particles in the liquid contact well with the methane bacteria and thus the organic solid particles can be readily decomposed, with the result that the decomposing speed of the organic materials is fast, and that the digestive tank can be minimized. Accordingly, according to the present invention, the apparatus can be installed at low cost, and the cost of producing the gas can be lowered. Further, the digestive efficiency can be extremely promoted, and thus the gas generating rate increases, resulting in that the residue may be reduced, and that the inorganic sludge residue most proper for the fertilizer can be obtained.

Further, according to the present invention, the carbon; nitrogen ratio can be controlled at will by mixing at least two kinds of different organic materials in the milling process by the mill means when the raw liquid for generating the methane gas is prepared, and hence the maintenance of the best decomposing conditions by the methane bacteria can readily be performed, with the result of increasing the gas quality (increases of purity and calorie) and the gas production amount.

Although the present invention has been described in its preferred embodiments, however, it is readily understood that various changes and modifications may be made in the invention without departing from the spirit and scope of the present invention.

What is claimed is:

1. A method for producing methane gas, comprising the steps of:
   grinding bean-curd refuse into fine particles of approximately 1-50 microns by grinding means which include a rotary disc and a fixed disc facing the rotary disc, a clearance between the discs being in a range of about 10-100 microns;
   adding water or organic suspension during the grinding, to prepare a slurry;
   feeding the thus-prepared slurry to a storage tank;
   deaerating the slurry in the storage tank to obtain raw liquid for generating methane gas in high concentration;
   after said deaerating step, feeding the raw liquid to a digestive tank; and
   treating the raw liquid in the digestive tank with anaerobic bacteria to generate and the methane gas.

2. The method of claim 1, comprising the additional steps of
   feeding the thus-treated liquid to a second digestive tank, and
   treating the liquid with anaerobic bacteria in the same.

3. The method of claim 1, wherein the water or organic suspension is added to provide a mixing ratio between the bean-curd refuse and water added to the slurry of about 1:4-1:20 by weight.

4. The method of claim 1, wherein a ratio between the water and the bean-curd refuse in the digestive tank is about 80:20 to 96:5 by weight.

5. The method of claim 1, wherein the grinding means are a colloid mill.

* * * * *